(12) United States Patent
Grier et al.

(10) Patent No.: US 10,222,315 B2
(45) Date of Patent: Mar. 5, 2019

(54) MACHINE-LEARNING APPROACH TO HOLOGRAPHIC PARTICLE CHARACTERIZATION

(71) Applicant: NEW YORK UNIVERSITY, New York, NY (US)

(72) Inventors: David G. Grier, New York, NY (US); Aaron Yevick, New York, NY (US); Mark Hannel, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/518,739

(22) PCT Filed: Oct. 12, 2015

(86) PCT No.: PCT/US2015/055154
§ 371 (c)(1),
(2) Date: Apr. 12, 2017

(87) PCT Pub. No.: WO2016/060995
PCT Pub. Date: Apr. 21, 2016

(65) Prior Publication Data
US 2017/0241891 A1   Aug. 24, 2017

Related U.S. Application Data

(60) Provisional application No. 62/063,260, filed on Oct. 13, 2014.

(51) Int. Cl.
*G01B 9/021* (2006.01)
*G01N 15/14* (2006.01)
(Continued)

(52) U.S. Cl.
CPC ..... *G01N 15/1429* (2013.01); *G01N 15/0227* (2013.01); *G01N 15/147* (2013.01);
(Continued)

(58) Field of Classification Search
CPC ........... G01N 15/1429; G01N 15/1434; G01N 15/147; G01N 15/1484; G01N 15/0227;
(Continued)

(56) References Cited

U.S. PATENT DOCUMENTS

6,519,033 B1   2/2003   Quist et al.
7,338,168 B2   3/2008   Cartlidge et al.
(Continued)

FOREIGN PATENT DOCUMENTS

WO   WO-2013/080164 A1   6/2013

OTHER PUBLICATIONS

Bishop, C.M., Neural Networks for Pattern Recognition, Dec. 31, 2015, p. 207, Oxford University Press, New York.
(Continued)

*Primary Examiner* — Tarifur R Chowdhury
*Assistant Examiner* — Jonathan Cook
(74) *Attorney, Agent, or Firm* — Foley & Lardner LLP

(57) ABSTRACT

Holograms of colloidal dispersions encode comprehensive information about individual particles' three-dimensional positions, sizes and optical properties. Extracting that information typically is computation-ally intensive, and thus slow. Machine-learning techniques based on support vector machines (SVMs) can analyze holographic video microscopy data in real time on low-power computers. The resulting stream of precise particle-resolved tracking and characterization data provides unparalleled insights into the composition and dynamics of colloidal dispersions and enables applications ranging from basic research to process control and quality assurance.

20 Claims, 3 Drawing Sheets

(51) Int. Cl.
*G01N 15/02* (2006.01)
*G01N 15/10* (2006.01)

(52) U.S. Cl.
CPC ..... *G01N 15/1434* (2013.01); *G01N 15/1484* (2013.01); *G01N 2015/0233* (2013.01); *G01N 2015/0238* (2013.01); *G01N 2015/1075* (2013.01); *G01N 2015/1445* (2013.01); *G01N 2015/1454* (2013.01); *G01N 2015/1477* (2013.01); *G01N 2015/1488* (2013.01); *G01N 2015/1493* (2013.01)

(58) Field of Classification Search
CPC ... G01N 2015/0233; G01N 2015/0238; G01N 2015/1445; G01N 2015/1477; G01N 2015/1488; G01N 2015/1493; G01B 9/02047; G01B 9/02083; G06N 99/005
USPC ....................................................... 356/457
See application file for complete search history.

(56) References Cited

U.S. PATENT DOCUMENTS

| | | | |
|---|---|---|---|
| 7,532,327 B2 | 5/2009 | Bloom et al. | |
| 8,791,985 B2 | 7/2014 | Grier et al. | |
| 9,933,351 B2* | 4/2018 | Kent | G01N 15/0612 |
| 2008/0037004 A1* | 2/2008 | Shamir | G01N 15/1459 356/73 |
| 2011/0043607 A1* | 2/2011 | Grier | G01N 15/0227 348/40 |
| 2011/0157599 A1 | 6/2011 | Weaver et al. | |
| 2012/0135535 A1 | 5/2012 | Grier et al. | |

OTHER PUBLICATIONS

Bourquard, A., et al., "A practical inverse-problem approach to digital holographic reconstruction", Opt. Express, Feb. 4, 2013, 21:3417-3433.

Chang, C-C., et al., "LIBSVM: A library for support vector machines", <http://www.csie.ntu.edu.tw/~cjlin/papers/libsvm.pdf>, initial version 2001 (updated Mar. 4, 2013), 1-39.

Chang, C-C., et al., "Training v-Support Vector Regression: Theory and Algorithms", Neural Comput., 2002, 14:1959-1977.

Cheong, F.C., et al., "Flow visualization and flow cytometry with holographic video microscopy", Opt. Express, Jul. 16, 2009, 17(15):13071-13079.

Cheong, F.C., et al., "Strategies for three-dimensional particle tracking with holographic video microscopy", Opt. Express, 2010, 18:13563-13573.

Dixon, L., et al., "Holographic particle-streak velocimetry", Opt. Express, Feb. 28, 2011, 19(5):4393-4398.

Fung, J., et al., "Holographic measurements of anisotropic three-dimensional diffusion of colloidal clusters", Phys. Rev. E, 2013, 88:020302-1-020302-5.

Grier, D., Downloadable holographic microscopy software written in IDL, the Interactive Data Language, <http://physics.nyu.edu/grierlab/software.html>, Sep. 16, 2014, 3 pages.

Krishnatreya, B.J., et al., "Fast feature identification for holographic tracking: the orientation alignment transform", Opt. Express, May 19, 2014, 22(11):12773-12778.

Krishnatreya, B.J., et al., "Measuring Boltzmann's constant through holographic video microscopy of a single sphere", Am. J. Phys., 2014, 82:23-31.

Lee, S-H., et al., "Characterizing and tracking single colloidal particles with video holographic microscopy", Opt. Express, Dec. 24, 2007, 15(26):18275-18282.

Lee, S-H., et al., "Holographic microscopy of holographically trapped three-dimensional structures", Opt. Express, 2007, 15:1505-1512.

Pedregosa, F., et al., "Scikit-learn: Machine Learning in Python", J. Mach. Learn. Res., 2011, 12:2825-2830.

Seifi, M., et al., "Fast and accurate 3D object recognition directly from digital holograms", J. Opt. Soc. Am. A, Nov. 2013, 30(11):2216-2224.

Sheng, J., et al., "Digital holographic microscope for measuring three-dimensional particle distributions and motions", Appl. Opt., Jun. 1, 2006, 45(16):3893-3901.

Shpaisman, H., et al., "Holographic microrefractometer", Appl. Phys. Lett., 2012, 101:091102-1-091102-3.

Smola, A.J., et al., "A tutorial on support vector regression", Stat. Comput., 2004, 14:199-222.

International Search Report and Written Opinion for Application PCT/US2015/015666, dated Jan. 7, 2016, 11 pages.

International Search Report and Written Opinion for Application PCT/US2015/055154, dated Jan. 7, 2016, 11 pages.

Extended European Search Report in EP 15792186.7, dated Dec. 14, 2017, 11 pages.

* cited by examiner

MACHINE-LEARNING APPROACH TO HOLOGRAPHIC PARTICLE CHARACTERIZATION

CROSS-REFERENCE TO RELATED APPLICATIONS

This application claims the benefit of U.S. Provisional Application No. 62/063,260 filed on Oct. 13, 2014, which is hereby incorporated by reference in its entirety.

GOVERNMENT INTEREST

The subject invention is subject to rights by the U.S. Government via the MRSEC program of the National Science Foundation under Grant No. DMR-0820341.

FIELD OF THE INVENTION

The invention is directed to a method and system for identification of features by holographic characterization. More particularly the invention is directed to a method and system for time accelerating of features identification by holographic characterization.

BACKGROUND OF THE INVENTION

Holographic microscopy records information about the spatial distribution of illuminated objects through their influence on the phase and intensity distribution of the light they scatter. This information can be retrieved from a hologram, at least approximately, by reconstructing the three-dimensional light field responsible for the recorded intensity distribution. Alternatively, features of interest in a hologram can be interpreted with predictions of the theory of light scattering to obtain exceedingly precise measurements of a scattering object's three-dimensional position, size and refractive index. The availability of so much high-quality information about the properties and motions of individual colloidal particles has proved a boon for applications as varied as product quality assessment, microrheology, porosimetry, microrefractometry, and flow velocimetry, as well as for molecular binding assays, and as a tool for fundamental research in statistical physics and materials science.

However, fitting measured holograms to theoretical predictions requires an initial for each scatterer's position. This can pose challenges for conventional image analysis algorithms because the hologram of a small object consists of alternating bright and dark fringes covering a substantial area in the field of view.

SUMMARY OF THE INVENTION

The foregoing summary is illustrative only and is not intended to be in any way limiting. In addition to the illustrative aspects, embodiments, and features described above, further aspects, embodiments, and features will become apparent by reference to the following drawings and the detailed description.

Holograms of colloidal dispersions encode comprehensive information about individual particles' three-dimensional positions, sizes and optical properties. Extracting that information typically is computationally intensive, and thus slow. Machine-learning techniques based on support vector machines (SVMs) can analyze holographic video microscopy data in real time on low-power computers. The resulting stream of precise particle-resolved tracking and characterization data provides unparalleled insights into the composition and dynamics of colloidal dispersions and enables applications ranging from basic research to process control and quality assurance.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 2. Tracking and characterizing a single colloidal sphere.

DETAILED DESCRIPTION OF THE PREFERRED EMBODIMENTS

Figure 1:
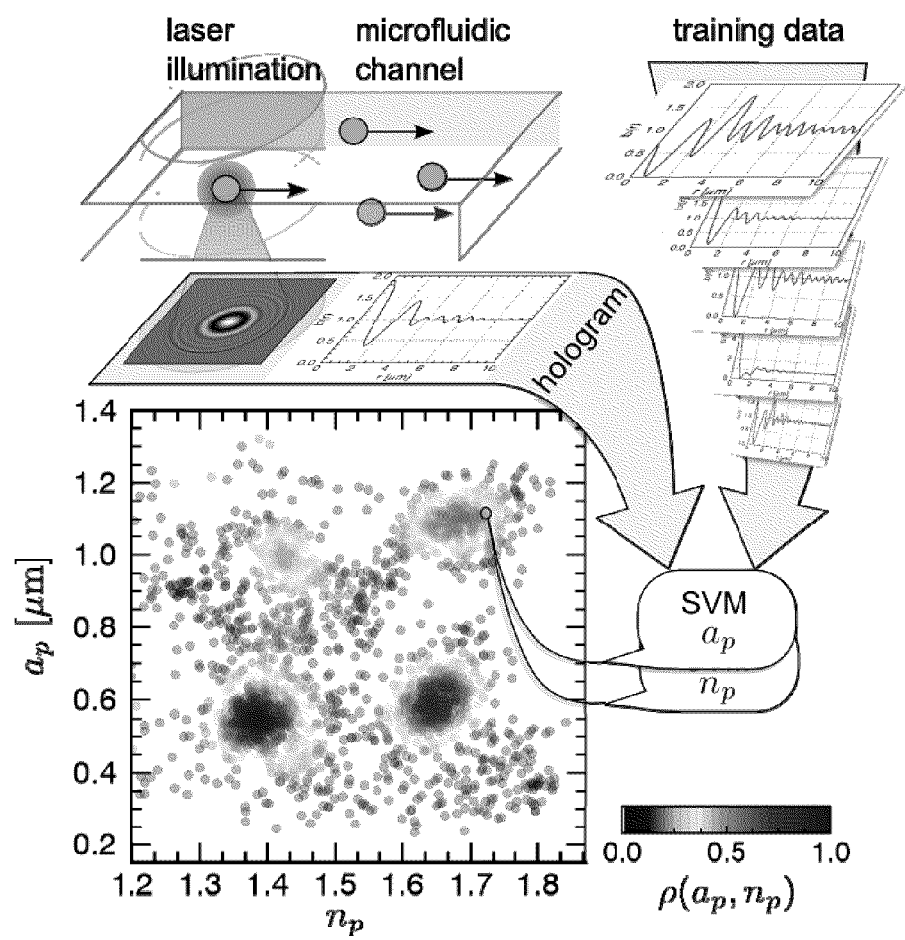
FIG. 1. Colloidal characterization by holographic microscopy and machine learning. Colloidal spheres flowing down a microfluidic sample scatter light from a collimated laser beam to form an in-line hologram. Features in the beam are identified, and their radial profiles presented to support vector machines (SVMs) that compare them with a library of training data to estimate each spheres' radius $a_p$ and refractive index $n_p$. The scatter plot shows results for 2,500 spheres drawn at random from a mixture of four different types of spheres. Each point is colored by the local density of data points, $\rho(a_p, n_p)$.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Holograms of colloidal spheres obtained with holographic video microscope can be interpreted with predictions of the Lorenz-Mie theory of light scattering to track each particle in three dimensions, and to measure its size and refractive index. State-of-the-art implementations can locate a sphere and resolve its radius both to within a few nanometers, and can determine its refractive index to within a part per thousand. The cost of this powerful technique is the computational burden of fitting each hologram pixel-by-pixel to theoretical predictions. Here, techniques of machine learning are demonstrated that can reduce the processing time by a factor of a thousand, yielding real-time performance.

One implementation to fast holographic characterization, depicted schematically in FIG. 1, employs the support vector machine (SVM) algorithm to compare experimental measurements with pre-computed predictions of the Lorenz-Mie theory. Whereas nonlinear fitting typically requires more than a second on a 1 Gflop computer, a trained SVM can estimate the size, refractive index or axial position of a micrometer-scale sphere in under a millisecond.

The in-line holographic microscope used for these studies illuminates the sample with a linearly polarized collimated laser beam (Coherent Cube, 20 mW) at a vacuum wavelength of $\lambda=447$ nm. The fluence of the 3 mm-diameter beam is comparable to that of a conventional microscope illuminator. Optical forces and light-induced heating therefore are negligible.

A collimated laser beam is input into the system. The laser beam is split into a reference beam and a scattering beam. The scattering beam is interacted with one or more colloidal particles to generate a scattered beam. The scattering beam, which is light scattered by a the colloidal particles, propagates to the focal plane of a video microscope where it interferes with the reference beam, which is undiffracted portion of the original input laser beam. The microscope magnifies this interference pattern onto the detector of a greyscale video camera, which records its intensity with a system magnification of 135 nm/pixel. Each snapshot in the video stream constitutes a hologram of the particles in the channel.

The electric field of the incident beam at position r in the focal plane may be modeled as a plane wave with spatial dependence $E_0(r) = u_0(r) e^{i\varphi_0(r)} e^{ikz} \hat{x}$, where $k = 2\pi n_m/\lambda$ is the wavenumber in a medium of refractive index $n_m$, and where $u_0(r)$ and $\varphi_0(r)$ account for small variations in the beam's amplitude and phase profiles, respectively.

A particle located at $r_p$ relative to the center of the focal plane scatters the incident illumination, $E_0(r_p)$, to the focal plane as $E_0(r_p) f_s(k(r-r_p)|a_p, n_p))$, where $f_s(kr|a_p, n_p)$ is the Lorenz-Mie scattering function that describes how a sphere of radius $a_p$ and refractive index $n_p$ scatters an $\hat{x}$-polarized plane wave. The measured intensity then may be modeled as $I(r) = |E_0(r) + E_s(r)|^2$. Normalizing the recorded hologram by $I_0(r) = |E_0(r)|^2 = u_0^2(r)$ suppresses spurious structure in the illumination and yields a functional form for the normalized hologram $$b(r) = \frac{I(r)}{I_0(r)} \approx |\hat{x} + e^{-ikz_p} f_s(k(r-r_p)|a_p, n_p)|^2, \quad (1)$$

that can be calculated with standard software packages.

Previous implementations of Lorenz-Mie microscopy fit Eq. (1) to measured holograms using $a_p$, $n_p$ and $r_p$ as adjustable parameters. These fits are exquisitely sensitive to errors in the particle's in-plane position, and so must be performed over the entire two-dimensional intensity distribution. Instead, Eq. (1) is used in one implementation to train support vector machines, which then are able to estimate $a_p$ (radius), $n_p$ (refractive index) and $z_p$ (axial position relative to the focal plane of the microscope) from a hologram's one-dimensional radial profile. These profiles are obtained from measured holograms by averaging around centers of rotational symmetry with single-pixel resolution, yielding 100-point data vectors. The associated reduction in dimensionality accounts in part for the implementation's computational efficiency. The two-dimensional position (x-y, in the plane of the hologram) is estimated. In one implementation of this procedure, the orientation alignment transform is used to coalesce the concentric-ring pattern of a sphere's hologram into a single bright peak, and then identify the position of the resulting feature with a standard peak-finding algorithm. Identifying this position with the center of the sphere's hologram, the median intensity is calculated at each of a range of single-pixel-wide radial bins centered on that position. The resulting azimuthal median average of the hologram's intensity distribution is an estimate for the hologram's radial profile, which then is supplied to a support vector machine for analysis.

The described SVMs are implemented with scikit-learn, an open-source machine learning software package that builds upon the libsvmlibrary of Support Vector Machine algorithms. Each SVM computes one output parameter from an input vector consisting of a radial profile, $b(r)$, that has been digitized into 100 single-pixel bins. Characterizing and tracking a colloidal particle therefore requires three SVMs, one for each of $a_p$, $n_p$ and $z_p$. FIG. 1 schematically represents this process for estimating $a_p$ and $n_p$.

An SVM computes its output by comparing $b(r)$ with sets of training data, $b_n(r)$, that are obtained from Eq. (1) over a range of values of $a_p$, $n_p$ and $z_p$. Each training set constitutes one support vector in the space spanned by these parameters. To facilitate these comparisons, construct SVMs with radial basis functions $(-\gamma \int |b_n(r) - b(r)|^2 dr)$ that quantify the similarity of the experimental input with the n-th support vector. The sensitivity of this comparison is set by $\gamma$, with larger values favoring more precise results at the cost of requiring more support vectors to span the parameter space. Given a value of $\gamma$, the training process determines a set of weights $\omega_n$ and an offset $s_0$ such that the weighted sum, $s_{fit}(b) = \Sigma_n \omega_n k_n(b) + s_0$, constitutes an estimate for the parameter, s. In general, errors in $s_{fit}(b)$ depend smoothly on $\gamma$. The optimal value for the present application is found to fall in the range $0.1 \leq \gamma \leq 10$.

To prevent overfitting, the weights w, are constrained to have magnitudes less than a maximum value that typically is denoted by C. Larger values of C improve an SVM's ability to recognize its training data, but render it less able to smoothly interpolate between its support vectors when presented with novel or noisy inputs. Some candidate support vectors may be assigned small weighting factors in optimizing $s_{fit}(b)$ over a corpus of training data; these are automatically eliminated from the SVM. Values of $\gamma$ and C thus determine which support vectors are included in the SVM, and their relative importance for computing the output. Because this process is nonlinear, optimal values of $\gamma$ and C are obtained by exhaustive search. Statistically indistinguishable results are obtained in the present application for values of $\gamma$ and C that vary from their optimal values by ten percent.

SVMs were trained with a 5,000-member training set whose parameters were evenly distributed over a volume in the three-dimensional space spanned by 13.5 $\mu m \leq z_p \leq 75$ $\mu m$, 0.4 $\mu m \leq a_p \leq 1.75$ $\mu m$, and $1.4 \leq n_p \leq 1.8$ at a resolution of 1.35 $\mu m$ in $z_p$, 0.1 $\mu m$ in $a_p$ and 0.1 in $n_p$. Values for C and $\gamma$ ranging from $10^{-3}$ to $10^5$ were selected for testing. Training time increases dramatically with the number of training sets, and with the values of C and $\gamma$. Once trained, however, each SVM can estimate its parameter extremely rapidly.

The quality of a trained SVM can be assessed by presenting it with novel cross-validation data. Optimal values for C and γ minimize differences between estimated parameters and the inputs. Using a 500-member cross-validation set, best performance was obtained for estimating $z_p$ with C=100 and γ=1, best performance for $n_p$ with C=10 and γ=0.5, and best performance for $a_p$ with C=10 and γ=0.6.

Sampling the entire parameter space accessible to holographic characterization with resolution comparable to the precision realized with nonlinear fits would require more than $10^{10}$ training sets. If, however, the system of interest is characterized by a more modest range of parameters, then results from an initial SVM analysis can be used to generate a comparatively small set of training data spanning the relevant range. This specialized training proceeds rapidly and yields substantial improvements in precision.

The data plotted in FIG. 1 are SVM estimates for the radii and refractive indexes of 2,500 colloidal spheres flowing down a microfluidic channel formed by bonding the edges of a glass microscope cover slip to the surface of a glass microscope slide. The peak flow speed of 1 mm/s transports a sphere across the field of view in no fewer than two video frames, ensuring that every particle in the flow has a chance to be analyzed. Anisotropic blurring due to a sphere's 100 nm motion during the camera's 0.1 ms exposure time suppresses contrast along the direction of motion, but does not appreciably influence the azimuthal average, b(r). Spurious results arising when multiple spheres' interference patterns overlap contribute outliers to the observed distribution of particle sizes and refractive indexes. Such artifacts are minimized by diluting the sample until no more than three particles are present in any frame.

The sample was prepared by dispersing roughly equal proportions of four types of colloidal spheres in water: 1 μm-diameter and 2 μm-diameter spheres made of polystyrene and silica. This four-component mixture was flowed through the observation volume during a 12 min interval, and analyzed particle-by-particle. Each data point in FIG. 1 corresponds to an individual sphere, and is colored by the local density of measurements.

SVM-mediated holographic characterization clearly identifies the four populations of particles without any a priori assumptions, and provides estimates for their relative abundances. Characterizing multicomponent dispersions is a unique capability of holographic particle analysis, and can be performed with SVMs as fast as particles' holograms can be acquired.

Neither the instrument nor the analytical technique requires extensive calibration. The wavelength of the laser and the effective magnification can be calibrated once and used for all samples. The refractive index of the medium is the only free parameter, and often can be obtained separately. These parameters are used to train the SVMs in advance, after which they can be used to analyze arbitrary samples dispersed in the medium.

Figures 2A, 2B, 2C:
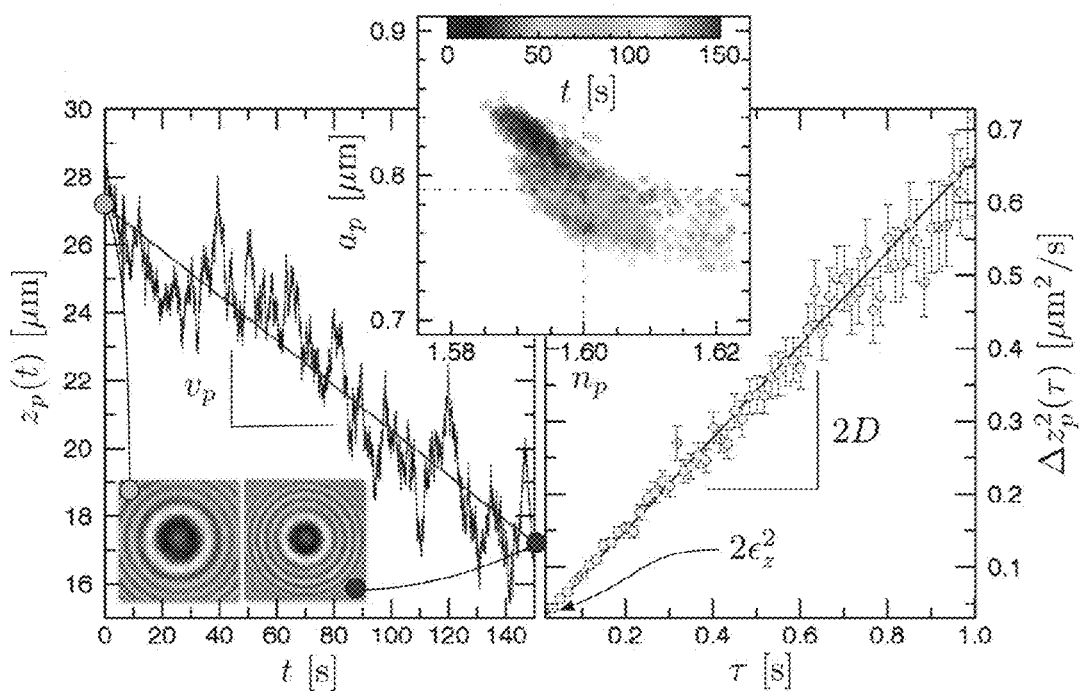
FIG. 2(a) The estimated axial position $z_p(t)$ relative to the focal plane of the microscope of a single polystyrene sphere sedimenting through water as it diffuses. The line is a least-squares fit. Insets show the sphere's hologram at the beginning and end of the trajectory.
FIG. 2(b) The radius $a_p$ and refractive index $n_p$ estimated from each hologram in the same sequence, colored by time. Each dot corresponds to values obtained from a single hologram.
FIG. 2(c) The mean-squared displacement, $\Delta z^2(\tau)$ as a function of lag time $\tau$ computed from the data in FIG. 2(a), including statistical error bars. The superimposed line is a fit to Eq. (2).

Tracking a single colloidal sphere as it sediments and diffuses provides insights into the precision and accuracy of SVM-mediated holographic characterization. The data in FIG. 2 were obtained with a 1.59 μm-diameter polystyrene sphere (Duke Scientific, catalog 4016A) diffusing as it sedimented through deionized water near the midplane of a 120 μm-deep channel. FIG. 2(a) shows the time-resolved trajectory, $z_p(t)$, obtained from a sequence of 4,500 video frames recorded at 29.97 frames/s using iterative SVM training.

Because polystyrene is roughly 5 percent more dense than water, the sphere sediments more than 10 μm over the course of the experiment. The insets to FIG. 2(a) show how markedly the hologram's appearance changes from the beginning of the trajectory to the end. Despite these changes, the SVMs' estimates for the radius and refractive index plotted in FIG. 2(b) remain clustered around the mean values $a_p$=0.79±0.02 μm and $n_p$=1.600±0.006.

Uncertainties in estimated parameters are computed as standard deviations of the distribution of results plotted in FIG. 2(b). These should be interpreted with care because errors in SVM estimates need not be independent or normally distributed. Data points in FIG. 2(b) cluster around different values as the particle descends, which suggests that different support vectors dominate the estimates for $a_p$ and $n_p$ when the sphere is at different axial positions. Systematic errors in the individual parameters therefore may vary with changes in any of the parameters' values. Even so, the averages of the SVM estimates are consistent with the manufacturer's specifications, and differ only slightly from those obtained with a full Lorenz-Mie analysis of the same data set, which yields $a_p$=0.805±0.001 μm and $n_p$=1.5730±0.0006. Nonlinear fitting offers ten times better precision and accuracy. SVM analysis is a thousand times faster.

The mean sedimentation speed, $v_p$=66±1 nm/s, estimated from the slope of $z_p(t)$ is somewhat smaller than the value measured with fits to the Lorenz-Mie theory of 75±1 nm/s. This discrepancy further suggests that the SVM estimate for a parameter's value may depend on the value itself. If it is assumed that errors in $z_p$ are normally distributed with a root-mean-square value $\varepsilon_z$, then the diffusing particle's mean-squared displacement should evolve over time interval τ as $$\Delta z_p^2(\tau) \equiv \langle [z_p(1+\tau)-z_p(1)]^2 \rangle , = 2D\tau + v_p^2\tau^2 + 2\varepsilon_z^2. \qquad (2)$$

where $D=k_BT/(6\pi\eta a_p)$ is the Stokes-Einstein value for the particle's diffusion coefficient. The data in FIG. 2(c) yield D=0.319±0.004 μm²/s, which is slightly larger than the value of 0.292±0.004 μm²/s obtained with the full Lorenz-Mie analysis. The best-fit tracking error, $\varepsilon_z$=107±2 nm, exceeds the Lorenz-Mie bound by an order of magnitude.

The results presented here are typical of the performance of SVMs for characterizing and tracking colloidal spheres. The speed and precision of SVM characterization is ideal for monitoring, feedback control and quality assurance in any industrial process involving colloidal spheres. Being able to resolve multimodal distributions by quickly amassing single-particle measurements avoids ambiguities inherent in population-averaging methods such as dynamic light scattering. Extracting the refractive index as well as the size offers insights into sample composition that otherwise would not be available. SVM-accelerated tracking can be used for real-time three-dimensional particle-image velocimetry. For applications such as microrefractometry, the medium's refractive index, nm, can be estimated instead of the particle's.

This combination of capabilities enables new applications. For example, the distribution of properties in colloidal mixtures could serve as fingerprints for complex fluid systems, with the sizes, refractive indexes and relative abundances encoding information that can be accessed with SVM-mediated holographic characterization. Thus, in one implementation colloidal fingerprinting includes adding a mixture of colloidal particles to a product, where the different types of particles differ in their radii and refractive indexes. Those properties are selected from distinct and distinguishable classes. As an example, the four-part mixture of large and small spheres made of silica and polystyrene described above. The presence or absence of different classes of spheres (e.g. large silica) can be used to embed information in the product. That information can be read out using the described holographic characterization techniques, including fast analysis with machine learning techniques (e.g. SVRs). Encoded information might include the date on which the product was created, the manufacturing location, the processing history, and so on. The colloidal "fingerprint" can be added to the product at the time of manufacturing without changing the other desirable properties of the product. This fingerprint then can be read-out at a later time by our method. No other single method would be able to distinguish all the properties of the dispersed particles at once, and thus no other method would be able to "read" the fingerprint. In one particular implementation, the fingerprinting could be used as an anti-counterfeiting measure. Further, the colloidal mixtures could be selected to have properties that vary over time such as due to breakdown of a compound to further provide a key for the fingerprint or act as another variable in the fingerprint.

Such applications can be realized with comparatively simple instruments conveying image data to low-power computers. Although training SVMs can be computationally intensive, the data comprising a set of trained SVMs occupies less than 100 Mbyte. Pre-computed SVMs therefore can be archived and rapidly retrieved when needed. This approach lends itself to implementation on embedded computers for integration into low-cost analytical instruments.

Other machine-learning techniques also might be effective for analyzing holograms of colloidal particles. Artificial neural networks, for instance, can be trained in the same manner as the present SVM implementation to interpret radial profiles of experimental holograms. SVMs have the advantage that their training process proceeds deterministically, and therefore tends to be faster. Once successfully trained, however, artificial neural networks are generally more computationally efficient. Regardless of implementation, the present results demonstrate that machine-learning methods facilitate fast and precise measurements of colloidal properties.

Figure 3:
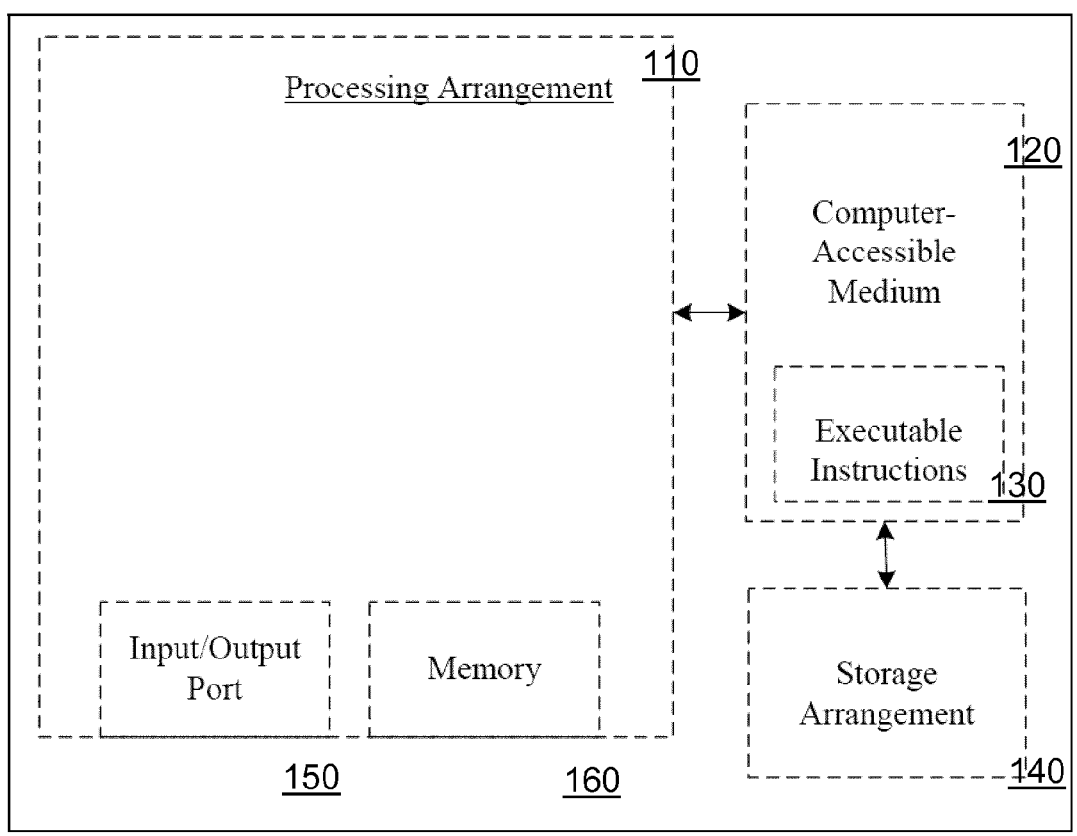
FIG. 3 illustrates a computer system for use with certain implementations.

As shown in FIG. 3, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed:

1. A method identifying a particle of interest comprising:
   inputting a collimated laser beam;
   splitting the beam into a diffracted beam and an undiffracted beam;
   interacting the diffracted beam with the particle of interest to generate a scattered beam;
   propagating the scattered beam to the focal plane of a microscope;
   interfering the propagated scattered beam with an undiffracted portion of the original beam
   recording a hologram characteristic of the scattering beam;
   obtain an estimated two-dimensional initial position of the particle of interest based upon a center of rotational symmetry in the recorded hologram;
   obtaining a radial profile of the hologram of the particle of interest using a machine learning algorithm to analyze the radial profile of the hologram of the particle of interest to obtain information about the particle of interest.

2. The method of claim 1, wherein the estimated initial position is determined from averaging around a center of rotational symmetry with single-pixel resolution.

3. The method of claim 1, wherein obtaining the radial profile of the hologram comprises averaging the recorded hologram of the particle of interest over angles in the focal plane around the estimated initial position to obtain a radial profile of the hologram of the particle of interest.

4. The method of claim 1, further comprising applying a machine learning algorithm to analyze the radial profile of the hologram of the particle of interest to obtain information about the particle of interest.

5. The method of claim 4 where the information is one of the axial position of the particle($z_p$), the radius of the particle ($a_p$,), and the refractive index of the particle($n_p$).

6. The method of claim 5, wherein each of the radius ($a_p$,), the refractive index ($n_p$), and the axial position relative to the focal plane of the microscope ($z_p$) are separately estimated by a different machine learning algorithm by comparing b(r) with sets of simulated data.

7. The method of claim 4 where the machine learning algorithm is a support vector machine.

8. The method of claim 6 where the simulated data is computed for values of the axial position of the particle, the radius of the particle and the refractive index of the particle that span respective desired range for each.

9. The method of claim 8, wherein a desired range for axial position of the particle $z_p$ is 13.5 µm≤$z_p$≤75 µm, a desired range for the radius of the particle $a_p$ is 0.4 µm≤$a_p$≤1.75 µm, and a desired range for the refractive index of the particle $n_p$ is 1.4≤$n_p$≤1.8.

10. The method of claim 9, wherein the resolution is 1.35 µm in $z_p$, 0.1 µm in $a_p$, and 0.1 in $n_p$.

11. The method of claim 8 where simulated data is provided to achieve a desired degree of convergence of the machine learning algorithm.

12. A method of identifying a property of a colloidal particle comprising:
   inputting a collimated laser beam;
   splitting the beam into a diffracted beam and an undiffracted beam;
   interacting the diffracted beam with the colloidal particle to generate a scattered beam;
   propagating the scattered beam to the focal plane of a microscope;
   interfering the propagated scattered beam with an undiffracted portion of the original beam
   recording a hologram characteristic of the scattering beam;
   determining an estimated initial position from averaging around a center of rotational symmetry with single-pixel resolution;
   averaging the recorded hologram of the particle of interest over angles in the focal plane around the estimated initial position to obtain a radial profile of the hologram of the particle of interest;
   using a machine learning algorithm to analyze the radial profile of the hologram of the colloidal particle to obtain information about the colloidal particle selected from the group consisting of axial position of the particle ($z_p$), radius of the particle ($a_p$,), and refractive index of the particle ($n_p$).

13. The method of claim 12, wherein each of the radius ($a_p$,), the refractive index ($n_p$), and the axial position relative to the focal plane of the microscope ($z_p$) are separately estimated by a different machine learning algorithm by comparing b(r) with sets of simulated data.

14. The method of claim 12 where the machine learning algorithm is a support vector machine.

15. The method of claim 13 where the simulated data is computed for values of the axial position of the particle, the radius of the particle and the refractive index of the particle that span respective desired range for each.

16. The method of claim 15, wherein a desired range for axial position of the particle $z_p$ is 13.5 µm≤$z_p$≤75 µm, a desired range for the radius of the particle $a_p$ is 0.4 µm≤$a_p$≤1.75 µm, and a desired range for the refractive index of the particle $n_p$ is 1.4≤$n_p$≤1.8.

17. The method of claim 16, wherein the resolution is 1.35 µm in $z_p$, 0.1 µm in $a_p$, and 0.1 in $n_p$.

18. A computer-implemented machine for identifying a particle of interest comprising, comprising:
   a processor; and
   a non-transitory computer-readable medium operatively connected to the processor and including computer code configured to:
   input a collimated laser beam;
   split the beam into a diffracted beam and an undiffracted beam;
   interact the diffracted beam with the particle of interest to generate a scattered beam;
   propagate the scattered beam to the focal plane of a microscope;
   interfere the propagated scattered beam with an undiffracted portion of the original beam
   record a hologram characteristic of the scattering beam;
   obtain an estimated two-dimensional initial position of the particle of interest based upon a center of rotational symmetry in the recorded hologram;
   obtain a radial profile of the hologram of the particle of interest; and
   use a machine learning algorithm to analyze the radial profile of the hologram of the particle of interest to obtain information about the particle of interest.

19. The computer implemented machine of claim 18, further comprising applying a machine learning algorithm to analyze the radial profile of the hologram of the particle of interest to obtain information about the particle of interest.

20. The computer implemented machine of claim 19 where the information is one of the axial position of the particle($z_p$), the radius of the particle ($a_p$,), and the refractive index of the particle($n_p$).

* * * * *